United States Patent
Ueda et al.

(10) Patent No.: US 8,241,677 B2
(45) Date of Patent: Aug. 14, 2012

(54) FOODSTUFF OF TABLETS OR CAPSULES

(75) Inventors: Fumitaka Ueda, Kanagawa (JP); Tomoko Mori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 12/676,305

(22) PCT Filed: Sep. 3, 2008

(86) PCT No.: PCT/JP2008/066267
§ 371 (c)(1),
(2), (4) Date: Mar. 3, 2010

(87) PCT Pub. No.: WO2009/031691
PCT Pub. Date: Mar. 12, 2009

(65) Prior Publication Data
US 2010/0196540 A1    Aug. 5, 2010

(30) Foreign Application Priority Data
Sep. 4, 2007 (JP) ................................. 2007-228615

(51) Int. Cl.
*A01N 65/00* (2009.01)
(52) U.S. Cl. ........................................................ 424/725
(58) Field of Classification Search .................. None
See application file for complete search history.

(56) References Cited

FOREIGN PATENT DOCUMENTS

| EP | 1 645 557 A1 | 4/2006 |
|---|---|---|
| EP | 1 674 106 A1 | 6/2006 |
| JP | 9-301862 A | 11/1997 |
| JP | 11152218 A | 6/1999 |
| JP | 2000-86653 A | 3/2000 |
| JP | 3030008 B2 | 4/2000 |
| JP | 2000159679 A | 6/2000 |
| JP | 2002-10752 A | 1/2002 |
| JP | 3261090 B2 | 2/2002 |
| JP | 2004-323420 A | 11/2004 |
| JP | 2005-21006 A | 1/2005 |
| JP | 2007037528 A | 2/2007 |
| JP | 2007097500 A | 4/2007 |

OTHER PUBLICATIONS

Yoshikawa, M., Food Style 21, May 2002, pp. 72-76, vol. 6, No. 5.
Japanese Patent Office, Communication dated Apr. 10, 2012 issued in corresponding Japanese Application No. 2007-228615.

*Primary Examiner* — Michael Miller
(74) *Attorney, Agent, or Firm* — Sughrue Mion, PLLC

(57) ABSTRACT

A foodstuff of a tablet or capsule, includes: an extract of a plant of genus *Salacia*; and at least one of calcium carbonate and silicon dioxide in an amount of 1% by mass or more based on the total mass of the tablet or capsule, wherein 50% inhibition concentration ($IC_{50}$ value) of sucrase is 10 μg/ml or more and 300 μg/ml or less.

7 Claims, 1 Drawing Sheet

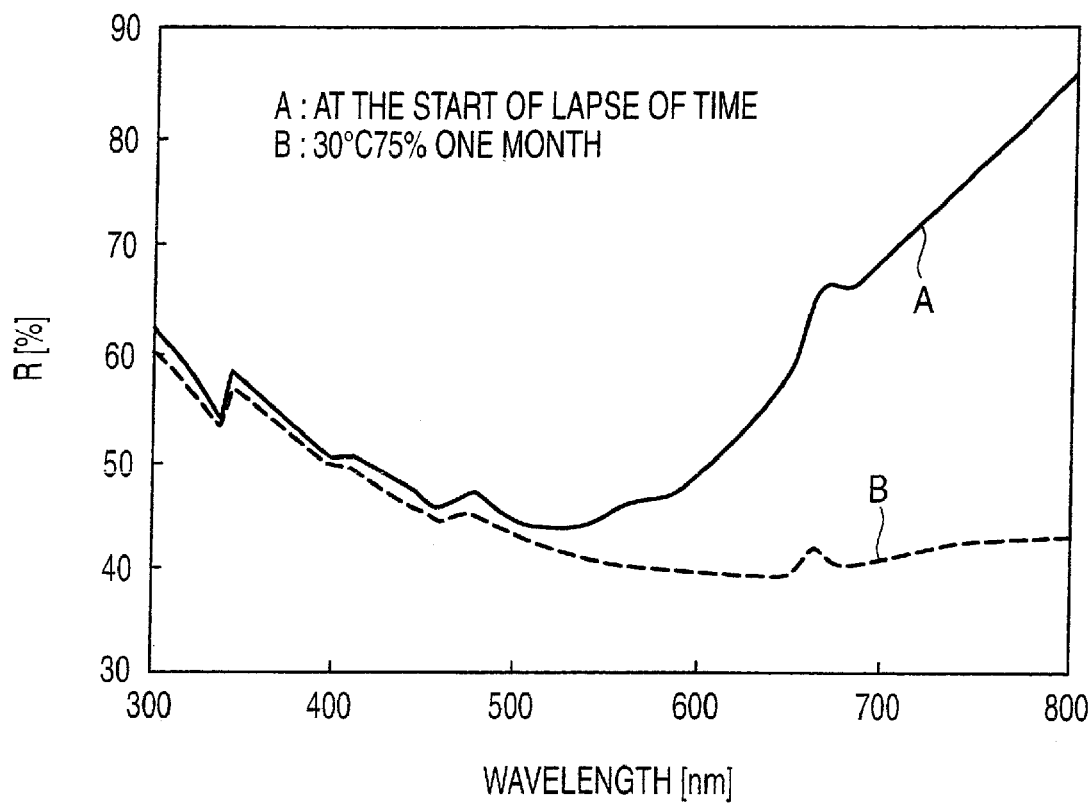

FOODSTUFF OF TABLETS OR CAPSULES

TECHNICAL FIELD

This invention relates to a foodstuff of tablets or capsules comprising an extract of a plant of the genus *Salacia*, wherein 50% inhibition concentration ($IC_{50}$ value) of sucrase is 10 µg/ml or more and 300 µg/ml or less.

BACKGROUND ART

The root and trunk of a plant of the genus *Salacia* have been used as a natural drug by a traditional medical science, aayurveda, in India and Sri Lanka. It has been handed down in Sri Lanka that the root skin of *Salacia reticulata* is effective in treating rheumatism, gonorrhea and a skin disease and is also used in the treatment of initial stage diabetes mellitus. In India, a root of *Salacia oblonga* is used in similar treatments, and it is said that *Salacia chinensis* is also used in the treatment of diabetes mellitus (FOOD Style 21, vol. 6, no. 5, pp. 72-78).

Thus, it has been handed down that plants of the genus *Salacia* are effective in the prevention and early stage treatment of diabetes mellitus. In recent years, it has been reported that a plant of the genus *Salacia* has the action to suppress increase of blood sugar value, and its action mechanism is the sugar absorption inhibitory action based on the α-glucosidase activity inhibition (FOOD Style 21, vol. 6, no. 5, pp. 72-78).

In addition, there are patents on the compounds which are contained in the extraction components of the genus *Salacia* and have the action to inhibit α-glucosidase activity (Japanese Patent No. 3030008, JP-A-2004-323420 and JP-A-2000-86653), and their application examples and patents as anti-diabetic agents based on the α-glucosidase activity inhibitory action (JP-A-9-301882 and Japanese Patent No. 3261090).

Since the circulating *Salacia* extract powder has the property to change color with the lapse of time, when the taking amount of tablets which contain the *Salacia* extract powder is decreased by increasing its blending amount per tablet, it exerts uneasiness and unpleasantness to consumers when ingested as food. Thus, there was a disadvantage in that the change of color must be covered by coloring it or using colored capsules.

On the other hand, when said blending amount per tablet is decreased in order to suppress the change of color, the sucrase inhibitory activity per grain becomes low (that is, the $IC_{50}$ value becomes large), so that the necessary number of tablets to be ingested becomes large which imposes a burden on the ingesting persons.

DISCLOSURE OF THE INVENTION

The invention contemplates providing a foodstuff of tablets or capsules comprising an extract of a plant of the genus *Salacia*, which unites reduction of ingesting amount and suppression of change in color.

As a result of carrying out intensive studies for the purpose of solving the above-mentioned problems, it was found that discoloration reaction is accelerated when tablets or capsules containing an extract of a plant belonging to the genus *Salacia*, which has high sucrase inhibitory activity (small $IC_{50}$ value), are contaminated with a very small amount of moisture. In addition, when an examination was carried out, with the aim of preventing this, on additive agents having the property to absorb moisture, it was discovered that calcium chloride and the like desiccants having deliquescence rather worsen the discoloration, and that periodical discoloration can be prevented when calcium carbonate or silicon dioxide having no deliquescence is contained therein in a total mass of 1% or more. (In this specification, mass ratio is equal to weight ratio.)

According to the invention, the burden on the ingesting persons is alleviated by supplying a stable product having high sugar absorption suppressing effect and less discoloration, through the supplement of tablets or capsules containing an extract of a plant belonging to the genus *Salacia*, which has high sucrase inhibitory activity (small $IC_{50}$ value), with the above-mentioned calcium carbonate or silicon dioxide in a total mass of 1% or more, and thereby minimizing the necessary amount of ingestion. In addition, minimization of the ingesting amount also renders possible broadening of the range of applications of the production and processing and suppression of the cost of products.

The exemplary embodiments of the present invention are described as follows.

(1) A foodstuff of a tablet or capsule, comprising:

an extract of a plant of genus *Salacia*; and at least one of calcium carbonate and silicon dioxide in an amount of 1% by mass or more based on the total mass of the tablet or capsule, wherein 50% inhibition concentration ($IC_{50}$ value) of sucrase is 10 µg/ml or more and 300 µg/ml or less.

(2) The foodstuff as described in (1) above, wherein 50% inhibition concentration ($IC_{50}$ value) of sucrase is 20 µg/ml or more and 250 µg/ml or less.

(3) The foodstuff as described in (1) or (2) above, wherein 50% inhibition concentration ($IC_{50}$ value) of sucrase is 30 µg/ml or more and 200 µg/ml or less.

(4) The foodstuff as described in any one of (1) to (3) above, wherein the plant of the genus *Salacia* is at least one plant selected from the group consisting of *Salacia reticulata, Salacia oblonga, Salacia prinoides* and *Salacia chinensis*.

(5) The foodstuff as described in any one of (1) to (4) above, wherein an amount of the calcium carbonate is 2.5% by mass or less based on the total mass of the tablet or capsule, and an amount of the silicon dioxide is 2.0% by mass or less based on the total mass of the tablet or capsule.

(6) The foodstuff as described in any one of (1) to (5) above, further comprising:

at least one low moisture absorption material selected from the group consisting of cellulose, crystalline cellulose, cellulose powder, microcrystalline cellulose, lactose, an oligosaccharide, a sugar alcohol, trehalose, magnesium stearate and calcium stearate.

(7) The foodstuff as described in (6) above, wherein the at least one low moisture absorption material is selected from the group consisting of crystalline cellulose, microcrystalline cellulose and lactose.

(8) The foodstuff as described in any one of (1) to (7) above, further comprising:

at least one moisture absorbent selected from the group consisting of silicates, magnesium carbonate, a ferrocyanide and polysaccharides.

BRIEF DESCRIPTION OF THE DRAWING

FIG. 1 is a graph showing reflection spectra before and after a lapse of time.

BEST MODE FOR CARRYING OUT THE INVENTION

According to the invention, by the use of tablets or capsules containing an extract of a plant belonging to the genus *Salacia* having high sucrase inhibitory activity, their effect can be obtained with a small amount when ingested as a foodstuff so that the burden on the ingesting persons is alleviated. In addition, when the product of the invention is prepared, its stability is also increased which becomes useful in terms of its production and processing.

The plant of the invention belonging to the genus *Salacia* is a plant of the family Celastraceae, which grows wild mainly in Sri Lanka, India and Southeast Asia, and more illustratively, at least one plant selected from *Salacia reticulata, Salacia oblonga, Salacia prinoides* and *Salacia chinensis* is used.

According to the invention, the extract of a plant of the genus *Salacia* means a pulverized product of such a plant or an extract powder extracted from a root, trunk, leaf, flower, fruit or the like edible part. One or more parts may be mixed and used. More preferably, an extract powder extracted from a root or trunk is used.

Said extract powder is obtained by drying a product extracted from the aforementioned edible part with a solvent. The extraction solvent may be selected from water, alcohols including methanol and ethanol, or mixed solvents of water with alcohols or ketones such as acetone. Preferably, water, an alcohol or a hydrous alcohol is used. More preferably, hot water or ethanol or hydrous ethanol is used. Regarding the alcohol concentration of the aforementioned hydrous alcohol, those having a concentration of from 30 to 90% by mass, preferably from 40 to 70% by mass, may be used.

As the drying method, spray drying, freeze drying and the like can be exemplified, though not limited thereto.

According to the invention, in order to improve periodical discoloration by the extract of the plant of the genus *Salacia*, 1% by mass or more of calcium carbonate or silicon dioxide is contained in forming tablets or capsules. Regarding the addition of calcium carbonate or silicon dioxide, each may be contained alone in an amount of 1% by mass or more, or calcium carbonate and silicon dioxide may be jointly contained as a total of 1% by mass or more.

In addition, in the case of food application, upper limit of the addition of calcium carbonate is restricted to 2.5% by mass by the food sanitation law, and that of silicon dioxide to 2.0% by mass.

Further, the invention can use a low moisture absorption material or moisture absorbent applicable as food or a food additive agent. Preferably, cellulose, crystalline cellulose, cellulose powder, microcrystalline cellulose, lactose, an oligosaccharide, a sugar alcohol, trehalose, magnesium stearate, calcium stearate or the like is used as the low moisture absorption material. As the moisture absorbent, silicates, magnesium carbonate, a ferrocyanide, polysaccharides or the like are used. More preferably, crystalline cellulose, microcrystalline cellulose or lactose is used as the low moisture absorption material.

A compound necessary for forming into the tablets or capsule of the invention, and the like may be optionally contained. As examples of such a compound, erythritol, maltitol, hydroxypropylcellulose, kaolin, talc and the like can be cited.

According to the invention, conventionally known means and conventionally known materials can be applied to the preparation method for forming tablets, granulation of capsule inclusion matter for forming capsules, capsulation, capsule material and the like.

The sucrase 50% inhibitory concentration ($IC_{50}$ value) of the food stuff of the invention is 10 µg/ml or more and 300 µg/ml or less, preferably 20 µg/ml or more and 250 µg/ml or less, more preferably 30 µg/ml or more and 200 µg/ml or less. When the inhibition activity becomes smaller than this, the absorption suppressing action of glucose from the digestive tracts becomes weak so that it is necessary to increase the number of ingesting tablets for obtaining the desired effect.

The sucrase 50% inhibitory concentration ($IC_{50}$ value) is measured by the following method.

[Test Method 1] Measurement of Sucrase $IC_{50}$ Value

Preparation of sample solution: A 2 mg portion of a sample is weighed and put into a tube and thoroughly suspended in 2 ml of water added thereto, thereby preparing a sample solution having a concentration of 1 mg/ml. This is diluted with water to respective concentrations of 0, 50, 100, 250 and 500 µg/ml.

Preparation of substrate liquid: Sucrose is dissolved in 0.2 M maleate buffer (pH 6.0) to a sucrose concentration of 100 mM, and this is used as the substrate liquid.

Preparation of crude enzyme liquid: A 1 g portion of intestinal acetone powder rat (mfd. by SIGMA) is suspended in 10 ml of physiological saline and then centrifuged (3,000 rpm, 4° C., 5 min). The thus obtained supernatant is separated and used as the crude enzyme liquid.

A 400 µl portion of the substrate liquid is added to 500 µl of each of the aforementioned sample solution having respective concentrations and preliminarily heated at 37° C. for 5 minutes in a water bath. A 100 µl portion of the crude enzyme liquid is added to each of them and allowed to undergo the reaction at 37° C. for 60 minutes. After completion of the reaction, the reaction is terminated by deactivating the enzyme through heating at 95° C. for 2 minutes. Determination of concentration of the thus formed glucose is carried out using a commercially available kit for mutarotase glucose oxidase method (Glucose CII Test Wako, mfd. by Wako Pure Chemical Industries).

Preparation of blank: A 200 µl portion of the substrate liquid and 50 µl of the crude enzyme liquid are added to 250 µl of each of the aforementioned sample solution having respective concentrations and immediately heated at 95° C. for 2 minutes to effect thermal deactivation of the enzyme, to be used as blank data.

By preparing a calibration curve from the thus obtained values, the concentration which inhibits 50% of the enzyme activity ($IC_{50}$ value) is calculated.

Embodiment

The following describes the invention based on examples, but the invention is limited to the following examples.

EXAMPLE 1

An extract powder was prepared by spray-drying a liquid obtained by pulverizing root and trunk parts of *Salacia reticulata* and *Salacia oblonga* and then passing through a hot water extraction step.

The powders having the following formulations were prepared using this extract powder, and the sucrase $IC_{50}$ value was measured by the method described in the [Test method 1].

TABLE 1

Salacia formulation examples and sucrase $IC_{50}$ value

| | Salacia extract powder | Crystalline cellulose | Calcium carbonate | Fine granule silicon dioxide | sucrase $IC_{50}$ value | |
|---|---|---|---|---|---|---|
| F.E. 1 | 200 mg | 0 mg | 0 mg | 0 mg | 81 | C.E. |
| F.E. 2 | 140 mg | 60 mg | 0 mg | 0 mg | 120 | C.E. |
| F.E. 3 | 100 mg | 100 mg | 0 mg | 0 mg | 155 | C.E. |
| F.E. 4 | 60 mg | 140 mg | 0 mg | 0 mg | 249 | C.E. |
| F.E. 5 | 50 mg | 150 mg | 0 mg | 0 mg | 292 | C.E. |
| F.E. 6 | 40 mg | 170 mg | 0 mg | 0 mg | 365 | C.E. |
| F.E. 7 | 60 mg | 138.5 mg | 1.5 mg | 0 mg | 250 | C.E. |
| F.E. 8 | 60 mg | 138.5 mg | 0 mg | 1.5 mg | 249 | C.E. |
| F.E. 9 | 60 mg | 138 mg | 2 mg | 0 mg | 248 | I.E. |
| F.E. 10 | 60 mg | 138 mg | 1 mg | 1 mg | 245 | I.E. |
| F.E. 11 | 60 mg | 136 mg | 0 mg | 2 mg | 246 | I.E. |
| F.E. 12 | 140 mg | 58 mg | 2 mg | 0 mg | 120 | I.E. |
| F.E. 13 | 200 mg | 0 mg | 2 mg | 2 mg | 83 | I.E. |

F.E.: Formulation Example,
C.E.: Comparative Example,
I.E.: Inventive Example

Reflection spectrum of the powder sample of Formulation 1 after a lapse of one month at 30° C. and at 75% RH was compared with that of the no lapse of time. The results are shown in FIG. 1.

When the sample of no lapse of time is compared with that of after a lapse of one month at 30° C. and at 75% RH, a change in the reflection spectrum can be seen so that the presence of discoloration can be seen.

Such a discoloration of powder was significantly found on the Formulation Examples 1 to 5, but hardly found in the case of the Formulation Examples 6 to 13.

EXAMPLE 2

Tablets 101 to 113 were obtained by subjecting the powders of Formulation Examples 1 to 13 of Example 1 to tablet making.

Respective tablets were stored at 30° C. and at 75% RH for 1 week, and absorbance on the tablet surface was measured.

The absorbance after storage is shown by a relative value when the absorbance before storage is regarded as 100.

In addition, the period of time until disintegration of the respective samples of tablets stored at 30° C. and at 75% RH for 1 week was measured in accordance with the disintegration test described in The Pharmacopoeia of Japan. Water was used as the solvent.

The disintegration time after storage is shown by a relative value when the disintegration time before storage is regarded as 100. The results are shown in Table 2.

TABLE 2

Discoloration and disintegration property of tablets after storage

| | Absorbance (relative value) after 1 week of storage at 30° C., 75% RH | Disintegration time (relative value) after 1 week of storage at 30° C., 75% RH | |
|---|---|---|---|
| Tablet 101 | 162 | 244 | Comparative Example |
| Tablet 102 | 148 | 205 | Comparative Example |
| Tablet 103 | 139 | 151 | Comparative Example |
| Tablet 104 | 131 | 143 | Comparative Example |
| Tablet 105 | 120 | 130 | Comparative Example |
| Tablet 106 | 102 | 101 | Comparative Example |
| Tablet 107 | 122 | 135 | Comparative Example |
| Tablet 108 | 125 | 140 | Comparative Example |
| Tablet 109 | 99 | 100 | Inventive Example |
| Tablet 110 | 100 | 100 | Inventive Example |
| Tablet 111 | 99 | 98 | Inventive Example |
| Tablet 112 | 101 | 101 | Inventive Example |
| Tablet 113 | 102 | 99 | Inventive Example |

As can be seen from the above data, it is evident that the tablets of the invention are superior to the comparative tablets, because their discoloration after the storage is small and delay of the disintegration time after storage cannot be found. Regarding the delay of disintegration time accompanied by discoloration, it is considered to be due to the formation of high molecular components caused by Maillard reaction and the like polymerization reactions.

In addition, according to the item "Neutral fat increase suppressing effect" described in the Food New Material Effective Application Technique Series NO. 18 "Kothala-him" 5-2), published by Confectionery General Technical Center, it is described that 400 mg of a powder having a sucrase inhibition activity value $IC_{50}$ of 120 is necessary for delaying increase of neutral fat in blood, and this means that the amount of the above-mentioned tablet for expecting the same effect is sufficient by two tablets of the tablet 112, but it is necessary to take seven tablets in the case of the tablet 106.

Accordingly, it is evident that the tablet 106 having an $IC_{50}$ value of 300 or more causes less discoloration, but is inferior in terms that the number of effective tablets which must be taken by once is larger than the tablets of the invention, which becomes a big burden.

EXAMPLE 3

Preparation of Tablets Using Extract Powder

By preparing tablets based on the formulation shown in Table 3, a shellac-coated supplement was prepared.

TABLE 3

Formulation example of tablets using the extract powder of the invention

| Raw material name | Blending amount (wt %) |
|---|---|
| Extract powder | 25.0 |
| Red wine polyphenol | 10.0 |
| Onion skin extract powder | 6.0 |
| Green tea extract | 15.0 |
| *Haematococcus* algal pigment | 1.0 |
| Chrome yeast | 4.0 |
| Carnitine | 10.0 |
| Crystalline cellulose | 23.0 |
| Sucrose fatty acid ester | 2.0 |
| Lactose | 1.0 |
| Calcium carbonate | 1.0 |
| Fine granule silicon dioxide | 2.0 |

Tablets which do not change color after a lapse of time were obtained by this formulation.

INDUSTRIAL APPLICABILITY

The invention attempts to alleviate the burden on the ingesting persons and also to obtain convenience in terms of the product processing of food, by the use of tablets or capsules comprising an extract of a plant of the genus *Salacia*, which has a high enzyme activity inhibitory action of 300 µg/ml or less as the 50% inhibition concentration ($IC_{50}$ value) of sucrase.

Also, when these are ingested as a foodstuff, the uneasiness and unpleasantness for ingestion due to discoloration are not exerted upon the ingesting persons, and their coloring or colored capsules become unnecessary. In addition, the invention can provide tablets which are excellent in disintegration property and have high sucrase inhibitory activity.

The entire disclosure of each and every foreign patent application from which the benefit of foreign priority has been claimed in the present application is incorporated herein by reference, as if fully set forth.

The invention claimed is:

1. A composition consisting essentially of:
    an extract of at least one plant selected from the group consisting of *Salacia reticulate, Salacia oblonga, Salacia prinoides*, and *Salacia chinensis*; and
    calcium carbonate and silicon dioxide in an amount of 1% by mass or more based on the total mass of the composition,
    wherein the composition has a 50% inhibition concentration ($IC_{50}$ value) of sucrase of 10 microgram/ml or more and 300 microgram/ml or less.

2. The composition of claim 1, wherein the composition has a 50% inhibition concentration ($IC_{50}$ value) of sucrase of 20 microgram/ml or more and 300 microgram/ml or less.

3. The composition of claim 1, wherein the composition has a 50% inhibition concentration ($IC_{50}$ value) of sucrase of 30 microgram/ml or more and 300 microgram/ml or less.

4. The composition of claim 1,
    wherein the amount of the calcium carbonate is 2.5% by mass or less based on the total mass of the composition, and
    the amount of the silicon dioxide is 2.0% by mass or less based on the total mass of the composition.

5. A composition consisting essentially of:
    an extract of at least one plant selected from the group consisting of *Salacia reticulate, Salacia oblonga, Salacia prinoides*, and *Salacia chinensis*;
    calcium carbonate and silicon dioxide in an amount of 1% by mass or more based on the total mass of the composition; and
    at least one low moisture absorption material selected from the group consisting of cellulose, crystalline cellulose, cellulose powder, microcrystalline cellulose, lactose, an oligosaccharide, a sugar alcohol, trehalose, magnesium stearate and calcium stearate;
    wherein the composition has a 50% inhibition concentration ($IC_{50}$ value) of sucrase of 10 microgram/ml or more and 300 microgram/ml or less.

6. The composition of claim 5, wherein the at least one low moisture absorption material is selected from the group consisting of crystalline cellulose, microcrystalline cellulose and lactose.

7. A composition consisting essentially of:
    an extract of at least one plant selected from the group consisting of *Salacia reticulate, Salacia oblonga, Salacia prinoides*, and *Salacia chinensis*;
    calcium carbonate and silicon dioxide in an amount of 1% by mass or more based on the total mass of the composition; and
    at least one moisture absorbent selected from the group consisting of silicates, magnesium carbonate, a ferrocyanide and polysaccharides;
    wherein the composition has a 50% inhibition concentration ($IC_{50}$ value) of sucrase of 10 microgram/ml or more and 300 microgram/ml or less.

* * * * *